United States Patent
Hileman

(12) 
(10) Patent No.: US 6,217,618 B1
(45) Date of Patent: Apr. 17, 2001

(54) TIBIAL KNEE COMPONENT WITH A MOBILE BEARING

(75) Inventor: Dale E. Hileman, Akron, IN (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/426,620

(22) Filed: Oct. 26, 1999

(51) Int. Cl.[7] .................................................. A61F 2/38
(52) U.S. Cl. ...................................... 623/20.33; 623/20.29
(58) Field of Search ............................. 623/20.14, 20.15, 623/20.21, 20.23, 20.28, 20.29, 20.13, 20.32, 20.33, 20.34

(56) References Cited

U.S. PATENT DOCUMENTS

| 4,085,466 | 4/1978 | Goodfellow et al. ............... 3/1.911 |
| 4,094,017 | 6/1978 | Matthews et al. .................. 3/1.911 |

(List continued on next page.)

FOREIGN PATENT DOCUMENTS

| 0 472 475 A2 | 7/1991 | (EP) | A61F/2/38 |
| 0 498 586 A1 | 1/1992 | (EP) | A61F/2/38 |
| 0 519 872 A1 | 6/1992 | (EP) | A61F/2/38 |
| 0 592 750 B1 | 12/1992 | (EP) | A61F/2/38 |
| 0 670 151 A2 | 1/1995 | (EP) | A61F/2/38 |
| 0 636 353 A1 | 2/1995 | (EP) | A61F/2/38 |
| 0 674 887 A1 | 3/1995 | (EP) | A61F/2/38 |
| 79.20563 | 8/1979 | (FR) | A61F/1/00 |
| 2702651 * | 9/1994 | (FR) . | |
| 2 277 034 | 10/1994 | (GB) | A61F/2/38 |
| 2 278 782 | 12/1994 | (GB) | A61F/2/38 |
| 2 280 375 | 2/1995 | (GB) | A61F/2/38 |
| 2 291 355 | 7/1995 | (GB) | A61F/2/38 |
| 2 291 355 | 1/1996 | (GB) | A61F/2/38 |
| 2 293 109 | 3/1996 | (GB) | A61F/2/38 |
| 2 304 051 | 3/1997 | (GB) | A61F/2/38 |
| 2 312 166 | 10/1997 | (GB) | A61F/2/38 |
| 2 312 167 | 10/1997 | (GB) | A61F/2/38 |
| 2 312 168 | 10/1997 | (GB) | A61F/2/38 |
| 2 312 377 | 10/1997 | (GB) | A61F/2/38 |
| 2 313 314 | 11/1997 | (GB) | A61F/2/38 |
| WO 95/22303 | 8/1995 | (WO) | A61F/2/38 |
| WO 95/25484 | 9/1995 | (WO) | A61F/2/38 |
| WO 95/27450 | 10/1995 | (WO) | A61F/2/38 |
| WO 95/30390 | 11/1995 | (WO) | A61F/2/38 |
| WO 96/01087 | 1/1996 | (WO) | A61F/2/38 |
| WO 96/03097 | 2/1996 | (WO) | A61F/2/38 |

OTHER PUBLICATIONS

The Mechanical Testing of a Sliding Meniscus Knee Prosthesis; R. J. Minns, B.Eng., M.Sc., Ph.D., J. Campbell, CH.B., M.Ch. (Ortho), FRCS. Clinical Orthopaedies, Nov.–Dec. 1978, vol. 137; pp. 268–275.

S–ROM® Modular Total Knee System; Joint Medical Products Corp; 1993.

TRA™ Knee System Design Rationale; Nov.1996; pp. 1–23.

(List continued on next page.)

Primary Examiner—David H. Willse
Assistant Examiner—Brian E Pellegrino
(74) Attorney, Agent, or Firm—Todd A. Dawson

(57) ABSTRACT

An orthopaedic knee component for implanting within a proximal tibia includes a tibial tray with a distally extending stem, a proximal tibial plateau and a post extending from the tibial plateau. The post defines an axis of rotation. An intermediate carrier has an opening in which the post is disposed. The carrier is pivotal about the axis of rotation. A bearing carried by the tibial tray has an articular bearing surface for engagement with a femoral component. The bearing has a recess in which the intermediate carrier is disposed. The projection, carrier and recess allow pivotal movement of the bearing relative to the tibial plateau about the axis of rotation.

10 Claims, 4 Drawing Sheets

U.S. PATENT DOCUMENTS

| | | | |
|---|---|---|---|
| 4,136,405 | 1/1979 | Pastrick et al. | 3/1.911 |
| 4,216,549 | 8/1980 | Hillberry et al. | 3/1.911 |
| 4,219,893 | 9/1980 | Noiles | 3/1.911 |
| 4,224,696 | 9/1980 | Murray et al. | 3/1.911 |
| 4,224,697 | 9/1980 | Murray et al. | 3/1.911 |
| 4,257,129 | 3/1981 | Volz | 3/1.911 |
| 4,262,368 | 4/1981 | Lacey | 3/1.911 |
| 4,301,553 | 11/1981 | Noiles | 3/1.911 |
| 4,309,778 | 1/1982 | Buechel et al. | 3/1.911 |
| 4,470,158 | 9/1984 | Pappas et al. | 3/1.911 |
| 4,586,933 | 5/1986 | Shoji et al. | 623/20 |
| 4,634,444 | 1/1987 | Noiles | 623/20 |
| 4,728,332 | 3/1988 | Albrektsson | 623/20 |
| 4,888,021 | 12/1989 | Forte et al. | 623/20 |
| 4,950,297 | 8/1990 | Elloy et al. | 623/20 |
| 5,011,496 | 4/1991 | Forte et al. | 623/20 |
| 5,080,675 | 1/1992 | Lawes et al. | 623/20 |
| 5,171,283 | 12/1992 | Pappas et al. | 623/20 |
| 5,194,066 * | 3/1993 | Van Zile | 623/20.15 |
| 5,271,747 | 12/1993 | Wagner et al. | 623/20 |
| 5,282,868 | 2/1994 | Bahler | 623/20 |
| 5,314,481 | 5/1994 | Bianco | 623/20 |
| 5,314,483 | 5/1994 | Wehrli et al. | 623/20 |
| 5,330,533 | 7/1994 | Walker | 623/20 |
| 5,344,460 | 9/1994 | Turanyi et al. | 623/20 |
| 5,358,527 | 10/1994 | Forte | 623/20 |
| 5,358,530 | 10/1994 | Hodorek | 623/20 |
| 5,358,531 | 10/1994 | Goodfellow et al. | 623/20 |
| 5,370,701 | 12/1994 | Finn | 623/20 |
| 5,387,240 | 2/1995 | Pottenger et al. | 623/20 |
| 5,395,401 | 3/1995 | Bahler | 623/20 |
| 5,413,604 | 5/1995 | Hodge | 623/20 |
| 5,413,608 | 5/1995 | Keller | 623/20 |
| 5,458,644 | 10/1995 | Grundei | 623/20 |
| 5,480,446 | 1/1996 | Goodfellow et al. | 623/20 |
| 5,549,689 | 8/1996 | Epstein et al. | 623/20 |
| 5,556,432 | 9/1996 | Kubein-Meesenburg et al. | 623/20 |
| 5,609,639 | 3/1997 | Walker | 623/20 |
| 5,609,644 | 3/1997 | Ashby et al. | 623/20 |
| 5,658,342 | 8/1997 | Draganich et al. | 623/20 |
| 5,683,468 | 11/1997 | Pappas | 623/20 |
| 5,702,466 | 12/1997 | Pappas et al. | 623/20 |
| 5,725,584 | 3/1998 | Walker et al. | 623/20 |
| 5,824,103 * | 10/1998 | Williams | 623/20.32 |
| 5,879,394 | 3/1999 | Ashby et al. | 623/20 |
| 5,928,286 * | 7/1999 | Ashby et al. | 623/20.33 |

OTHER PUBLICATIONS

New Jersey LCS® Total Knee System; DePuy; 1994.

SAL Self–Aligning Total Knee Replacement; Protek.

Difficulties With Bearing Dislocation and Breakage Using a Movable Bearing Total Knee Replacement System; James K. Weaver, M.D., Robert S. Kerkash, M.D., A. Seth Greenwald D. Phil. (Oxon); Clinical Orthopaedics and Related Research. Number 290: pp. 244–252: 1993 J. B. Lippincott Company.

The Sliding Meniscus Knee Prosthesis: Design Concepts; R. J. Minns, J. Campbell.

The Design and BioMechanics of a Sliding Meniscus Knee Prothesis; R. J. Minns; pp. 306–309.

The Oxford Meniscal Knee Phase II; Biomet Ltd.; British JBJS, May 1988.

New Jersey Tricompartmental Total Knee System with Porocoat Surgical Procedure; Frederick F. Buechel, M.D.; DePuy.

New Jersey LCS ™Total Knee System with Porocoat; DePuy; JBJS vol. 67–A, No. 8; Oct. 1985.

AGC Total Knee System; Biomet Ltd., British JBJS; Nov. 1985.

Minns Meniscal Knee–A Total Prosthesis for Early Joint Degeneration; Zimmer (Swindon).

Gliding Meniscal Knee–A Major Development in Cruciate–Retaining Arthroplasty; Zimmer (Swindon).

Longer Implant Life in Three Easy Lessons; JBJS–Jul. 1998; DePuy.

SAL. Self–Aligning. An Evolution in Motion; Protek; JBJS Oct. 1997.

In 1977, The LCS™ Changed the Way Knees Work; Brit JBJS, Mar. 1997; DePuy.

Study the Facts–The Oxford™ Knee; British JBJS Mar. 1998; Biomet Ltd.

Longer Implants Life in Three Easy Lessons; JBJS–Jul. 1998; DePuy.

* cited by examiner

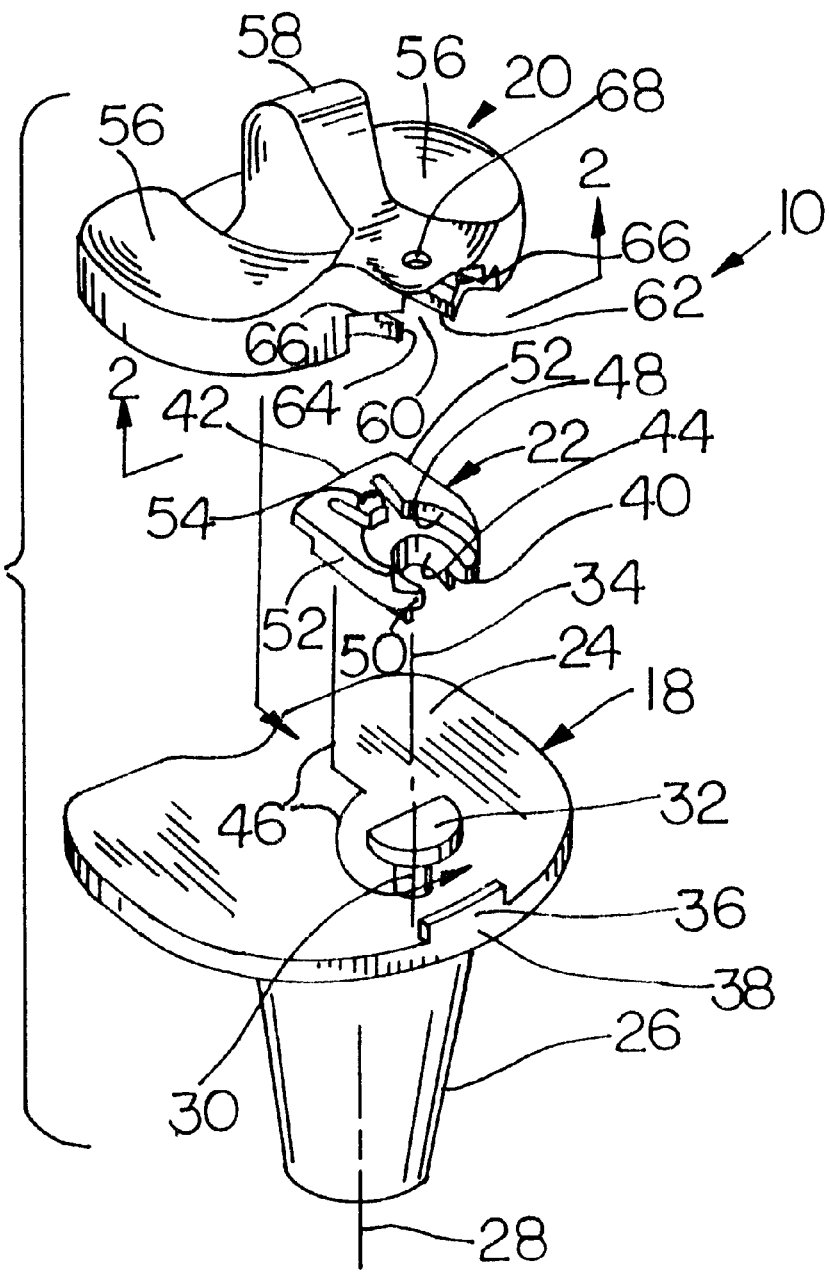
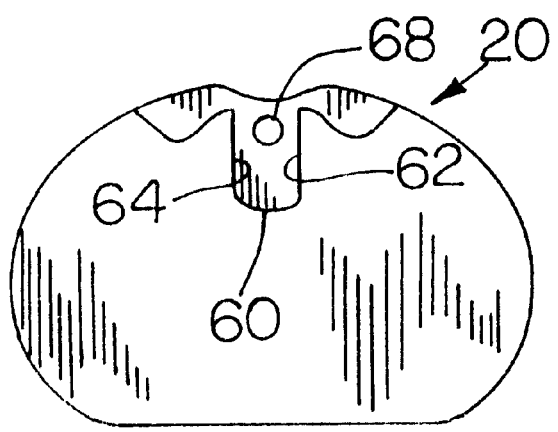

TIBIAL KNEE COMPONENT WITH A MOBILE BEARING

BACKGROUND OF THE INVENTION

1. Field of the Invention

The present invention relates to an orthopaedic implant, and, more particularly, to a tibial knee component.

2. Description of the Related Art

A tibial knee component is implanted within a proximal tibia and engages with a femoral component implanted within a distal femur. The tibial knee component typically includes a bearing which is immovably affixed to a tibial tray. The tibial tray includes a stem which is implanted within the intramedullary (IM) canal in the proximal tibia. The bearing may be in the form of a wear resistant and low friction material such as ultra high molecular weight polyethylene (UHMWPE) which is immovably attached to the tibial tray. Pivotal movement between the femoral component and the bearing surface of the bearing occurs with relatively low friction and low wear characteristics.

It is also known to provide a mobile bearing which moves relative to the tibial tray. During deep flexion between the femur and tibia, the bearing rotates about a longitudinal axis associated with a pivot point at the attachment location between the bearing and tibial tray. While some designs allow for 360 degrees of rotation between the mobile bearing and the tibial tray, most designs have a rotational limit provided. Although known designs are adequate to allow limited rotation between the bearing and tibial tray, they may be relatively complex and thus expensive to manufacture.

What is needed in the art is a tibial knee component with a mobile bearing which is easier to manufacture and still allows adequate movement between the bearing and tibial tray during deep flexion of the knee joint.

SUMMARY OF THE INVENTION

The present invention provides a tibial knee component with a tibial tray, intermediate carrier and bearing which interconnect together and allow pivotal movement between the bearing and tibial tray.

The invention comprises, in one form thereof, an orthopaedic knee component for implanting within a proximal tibia. A tibial tray includes a distally extending stem, a proximal tibial plateau and a post extending from the tibial plateau. The post defines an axis of rotation. An intermediate carrier has an opening in which the post is disposed. The carrier is pivotal about the axis of rotation. A bearing carried by the tibial tray has an articular bearing surface for engagement with a femoral component. The bearing has a recess in which the intermediate carrier is disposed. The projection, carrier and recess allow pivotal movement of the bearing relative to the tibial plateau about the axis of rotation.

An advantage of the present invention is that the bearing is free to pivot relative to the tibial tray about an axis of rotation.

Another advantage is that the bearing is inhibited from moving in an axial direction relative to the axis of rotation.

Yet another advantage is that the keeper block inhibits radial movement of the carrier relative to the post.

A further advantage is that the carrier includes a deflectable ramp which inhibits radial movement of the bearing relative to the post.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is an exploded, perspective view of an embodiment of an orthopaedic knee component of the present invention;

FIG. 2 is a bottom view of the bearing of FIG. 1 as viewed along line 2—2;

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 7:
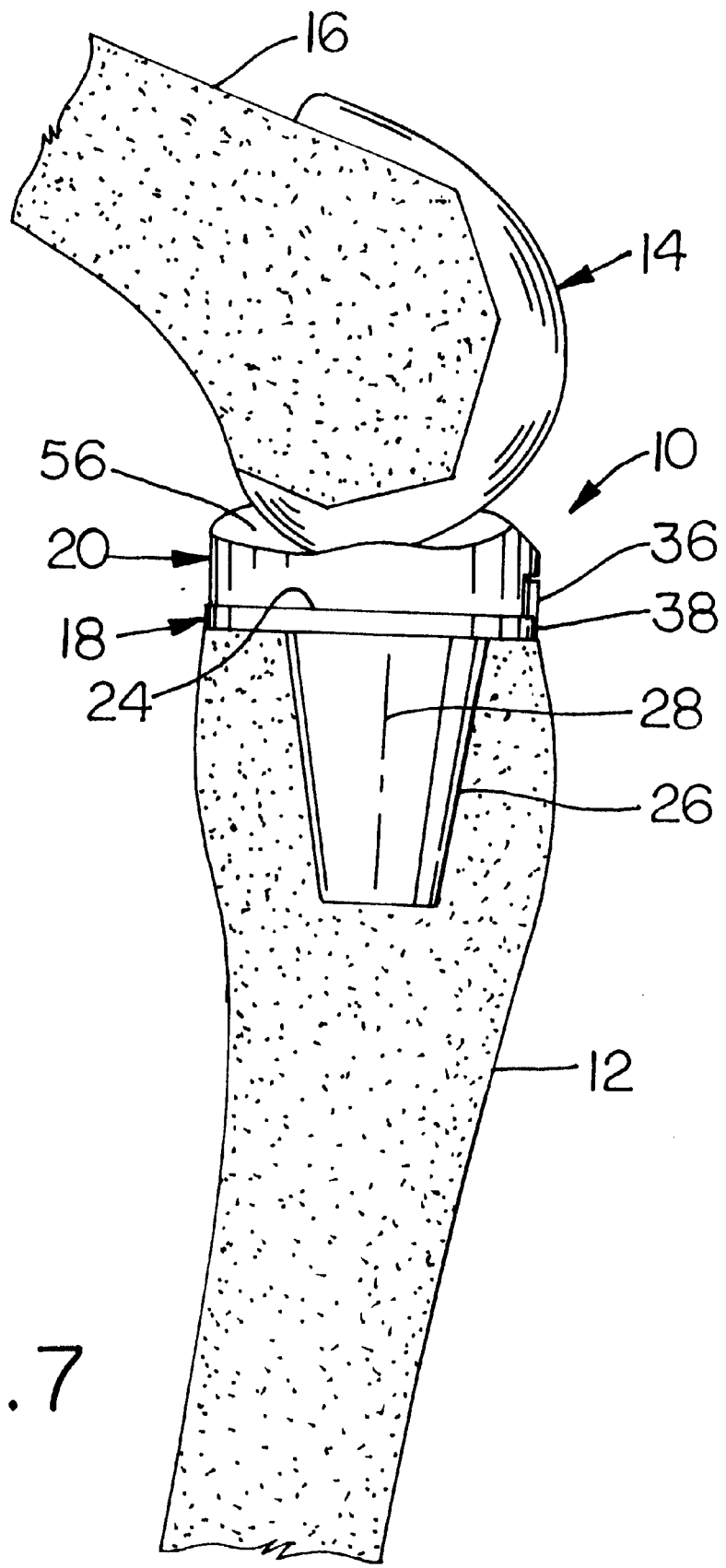
FIG. 7 is a side view of the orthopaedic knee component of FIGS. 1 and 3–6, implanted within a tibia and engaged with a femoral component.

Referring to the drawings, there is shown an embodiment of an orthopaedic knee component in the form of a tibial knee component 10 (FIG. 1) which is implanted within a proximal tibia 12 (FIG. 7). Tibial knee component 10 engages with a femoral component 14 which is implanted within a distal femur 16.

Tibial knee component 10 includes a tibial tray 18, bearing 20 and intermediate carrier 22. Tibial tray 18 has a proximal tibial plateau 24 and a distally extending stem 26. Tibial plateau 24 has a generally planar proximal surface which extends transverse (e.g., generally orthogonal) to a longitudinal axis 28 of stem 26. A generally cylindrically shaped post 30 with a retainer 32 has an axis of rotation 34 which extends generally orthogonal to tibial plateau 24, and thus also extends generally parallel to axis 28 of stem 26. Tibial tray 18 also includes a keeper block 36 positioned adjacent to an anterior ledge 38. Keeper block 36 extends from tibial plateau 24 and inhibits movement of carrier 22 in a radial direction relative to post 30, as will be described in more detail hereinafter. Retainer 32 includes a radially extending flange which inhibits movement of intermediate carrier 22 in a direction generally parallel to axis of rotation 34.

Figure 3:
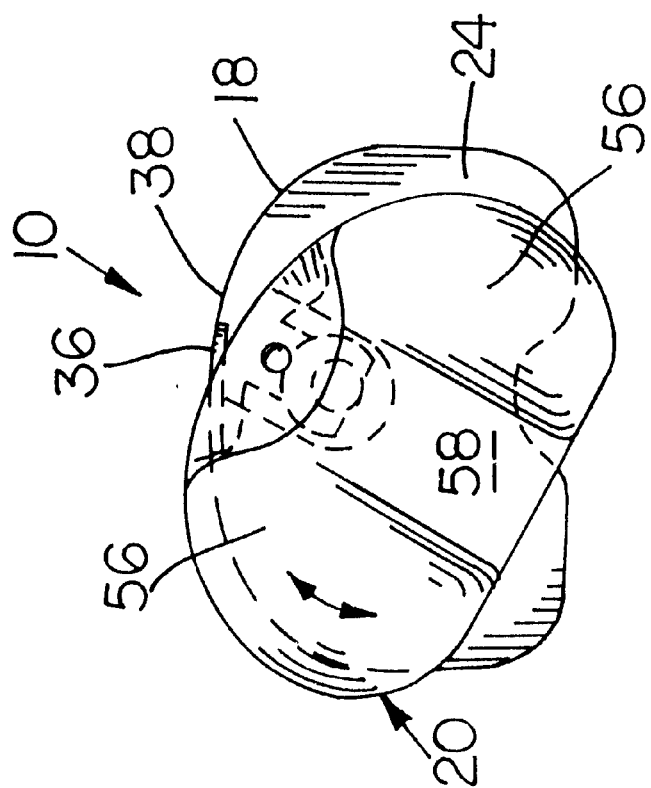
FIG. 3 is a top view of the orthopaedic knee component of FIG. 1, with the bearing in a neutral position.
Figure 4:
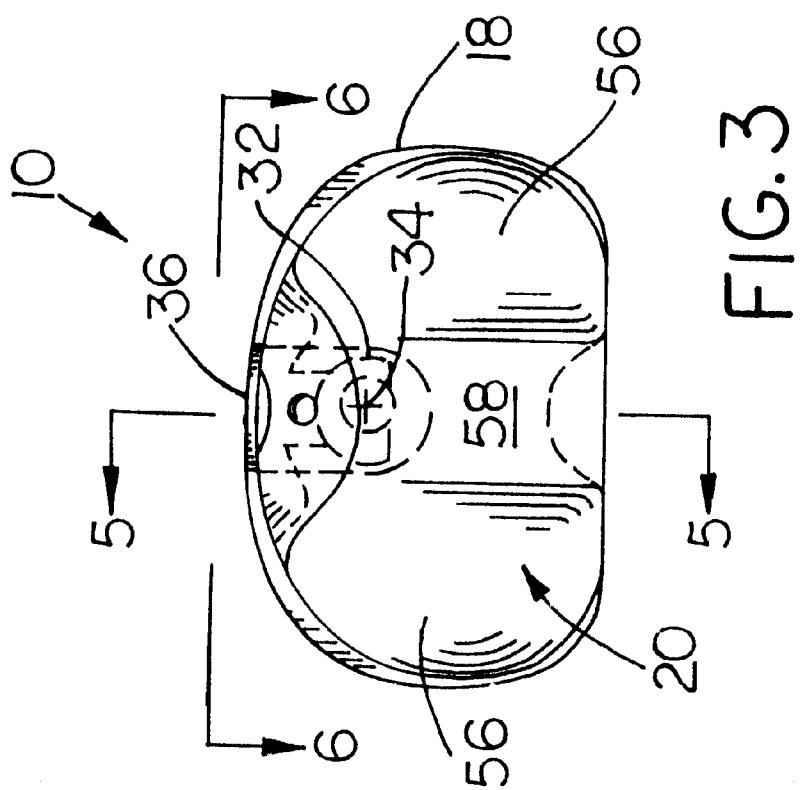
FIG. 4 is a top view of the orthopaedic knee component of FIG. 1, with the bearing in a rotated position.
Figure 6:
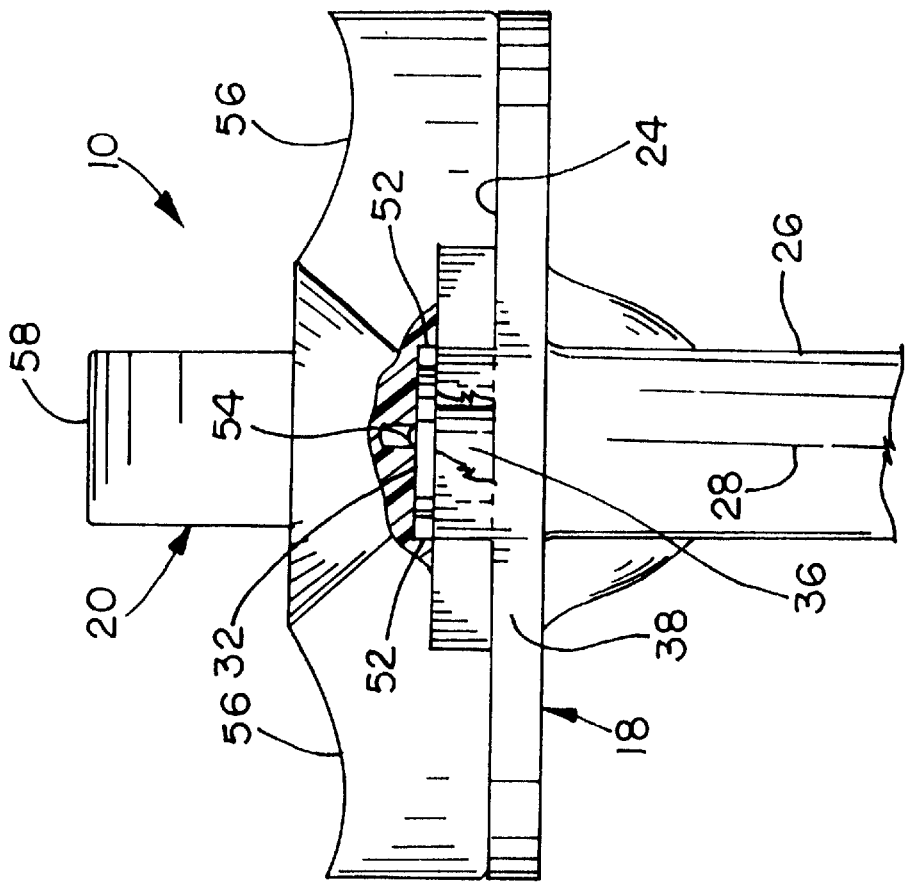
FIG. 6 is a fragmentary, front, partially sectioned view taken along line 6—6 in FIG. 3.
Figure 5:
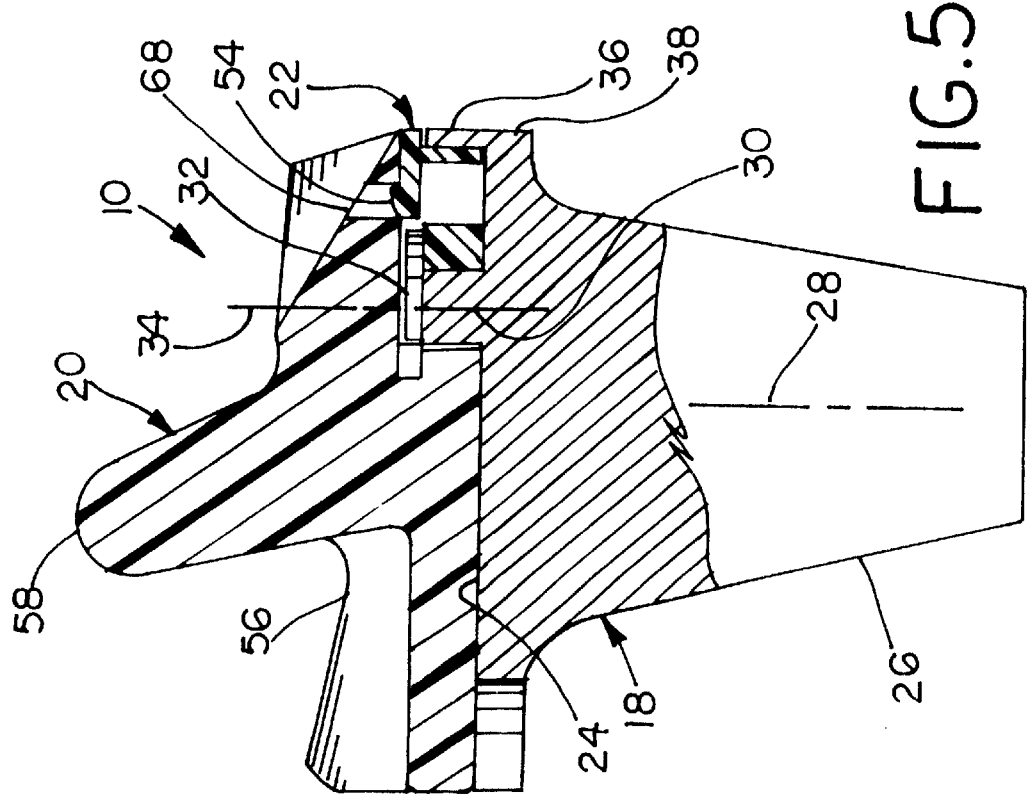
FIG. 5 is a fragmentary, side, partially sectioned view taken along line 5—5 in FIG. 3.

Intermediate carrier 22 has a longitudinal extension which extends between two longitudinally opposite ends 40, 42. An opening 44 is disposed adjacent to and in communication with end 40. Opening 44 has a diameter which corresponds to and is just slightly larger than the diameter of post 30. Post 30 is received within opening 44 such that intermediate carrier 22 is pivotable about axis of rotation 34, as indicated by assembly lines 46. Intermediate carrier 22 also includes a recess 48 positioned axially adjacent to opening 44. Recess 48 is sized and configured to receive retainer 32 therein when post 30 is positioned within opening 44 (FIGS. 5 and 6).

Intermediate carrier 22 also includes two side walls 50 which extend between first end 40 and second end 42. Each side wall 50 has an outwardly extending flange 52 which engages with bearing 20 and inhibits relative movement between bearing 20 and intermediate carrier 22 in a direction generally parallel to axis of rotation 34, as will be described in more detail hereinafter.

Intermediate carrier 22 further includes a deflectable ramp 54. Ramp 54 is of cantilever construction (FIG. 5) and thus may be deflected in a direction away from bearing 20 when intermediate carrier 22 is coupled with bearing 20. Ramp 54 retains intermediate carrier 22 with bearing 20 and inhibits relative movement therebetween in a radial direction relative to axis of rotation 34.

Bearing 20 has an articular bearing surface 56 for engagement with femoral component 14. Articular bearing surface 56 is disposed on either side of a center projection 58. Each discrete portion of articular bearing surface 56 on either side of center projection 58 engages a corresponding condyle of femoral knee component 14, with center projection 58 being disposed between the condyles. Bearing 20 also includes a generally slot shaped recess 60 in which intermediate carrier 22 is slidably disposed. Slot shaped recess 60 includes a first wall 62 and a second wall 64 which are positioned generally parallel to each other. First wall 62 and second wall 64 each include an undercut 66 which extends generally away from slot shaped recess 60. Each undercut 66 is sized and shaped to receive a corresponding flange 52 of intermediate carrier 22 therein. When coupled together, flanges 52 and undercuts 66 inhibit movement of bearing 20 relative to intermediate carrier 22 in a generally axial direction relative to axis of rotation 34.

Bearing 20 also includes a hole 68 positioned in communication with slot shaped recess 60. Hole 68 is located within bearing 20 such that deflectable ramp 54 is received therein when intermediate carrier 22 is slid to a fully seated position within bearing 20. Since hole 68 extends through bearing 20 and is not a blind hole within bearing 20, any fluid which may accumulate within hole 68 is free to exit therefrom without building up pressure.

To assemble tibial knee component 10, intermediate carrier 22 is positioned against tibial plateau 24 in the orientation shown in FIG. 1. Intermediate carrier 22 is then slid in a direction toward post 30 such that post 30 is received within opening 44. Intermediate carrier 22 is then rotated about axis of rotation 34 until second end 42 is positioned adjacent keeper block 36. Retainer 32 inhibits movement of intermediate carrier 22 in an axial direction relative to axis of rotation 34, while post 30 and keeper block 36 inhibit movement of intermediate carrier 22 in a radial direction relative to axis of rotation 34. Bearing 20 is then positioned against tibial plateau 24 adjacent first end 40 of intermediate carrier 22. Intermediate carrier 22 is slid into slot shaped recess 60 of bearing 20, such that flanges 52 are retained within undercuts 66. At a fully seated position, deflectable ramp 54 projects into hole 68 and thus inhibits sliding movement between bearing 20 and intermediate carrier 22 (i.e., in a direction radial to axis of rotation 34). Tibial knee component 10 may then be implanted within a prepared proximal tibia. Of course, it will be appreciated that tibial tray 18 may be implanted within the proximal tibia when disassembled from intermediate carrier 22 and bearing 20. That is, intermediate carrier 22 and bearing 20 may be assembled with tibial tray 18 after tibial tray 18 is implanted within proximal tibia 12.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic knee component for implanting within a proximal tibia, comprising: a tibial tray including a distally extending stem, a proximal tibial plate and a post extending from said tibial plate proximally from said tibial plate, said post defining an axis of rotation coincident with a longitudinal axis of said post;

an intermediate carrier having an opening, said post received within said opening and said intermediate carrier pivotal about said axis of rotation; and a bearing carried by said tibial tray and having an articular bearing surface for engagement with a femoral component, said bearing having a recess in which said intermediate carrier is disposed, said post, intermediate carrier and recess allowing pivotal movement of said bearing relative to said tibial plateau about said axis of rotation, wherein said recess is generally slot shaped and said intermediate carrier is slidably disposed within said recess, and wherein said bearing includes a hole and said intermediate carrier includes a deflectable ramp positioned within said hole.

2. The orthopaedic knee component of claim 1, wherein said deflectable ramp is of cantilever construction.

3. The orthopaedic knee component of claim 1, wherein said post includes a radially extending flange inhibiting movement of said carrier in a direction generally parallel to said axis of rotation.

4. The orthopaedic knee component of claim 1, wherein said recess includes a first wall and a second wall generally parallel to each other, said first wall and said second wall including an undercut, said carrier including at least one outwardly extending flange extending into said undercut.

5. The orthopaedic knee component of claim 4, wherein each said flange and said undercut define a means for inhibiting movement of said bearing relative to said carrier in a direction generally axial to said axis of rotation.

6. The orthopaedic knee component of claim 4, wherein each of said first wall and said second wall include an undercut, and said projection includes two flanges which respectively extend into a corresponding said undercut.

7. The orthopaedic knee component of claim 1, wherein said tibial plate includes an anterior ledge and a keeper block extending from said tibial plateau adjacent said anterior ledge, said carrier disposed between said post and said keeper block.

8. The orthopaedic knee component of claim 7, wherein said keeper block defines a means for preventing movement of said carrier in a radial direction relative to said post.

9. The orthopaedic knee component of claim 1, wherein said carrier is substantially immovable relative to said bearing in a direction generally parallel to said axis of rotation.

10. The orthopaedic knee component of claim 9, wherein said carrier is substantially immovable relative to said bearing in a rotative direction relative to said axis of rotation.

* * * * *